United States Patent [19]
Bond et al.

[11] Patent Number: 5,308,358
[45] Date of Patent: May 3, 1994

[54] RIGID-SHAFT SURGICAL INSTRUMENTS THAT CAN BE DISASSEMBLED FOR IMPROVED CLEANING

[76] Inventors: Albert L. Bond, Rte. 1, Box 146, Patterson, Mo. 63956; George W. Doerr, III, 410 May Valley, Apt. F, Fenton, Mo. 63026; John M. Mayerik, Jr., 12434 Matthews La., St. Louis, Mo. 63127

[21] Appl. No.: 935,525

[22] Filed: Aug. 25, 1992

[51] Int. Cl.5 .............................. A61B 17/42
[52] U.S. Cl. .................. 606/205; 606/170; 606/174; 606/207
[58] Field of Search ............ 128/751, 752, 753, 754, 128/755; 604/22; 606/37, 39, 45, 46, 51, 52, 79, 167, 170, 171, 174, 205

[56] References Cited

U.S. PATENT DOCUMENTS

| | | | |
|---|---|---|---|
| 2,790,437 | 10/1955 | Moore | 606/170 |
| 4,122,856 | 10/1978 | Mosior et al. | 606/174 |
| 4,262,676 | 4/1981 | Jamshidi | 128/753 |
| 4,662,371 | 5/1987 | Whipple et al. | 606/174 |
| 4,813,407 | 3/1989 | Vogen | 606/151 |
| 5,009,661 | 4/1991 | Michelson | 606/170 |
| 5,141,519 | 8/1992 | Smith et al. | 606/170 |
| 5,147,357 | 9/1992 | Rose et al. | 606/52 |

Primary Examiner—C. Fred Rosenbaum
Assistant Examiner—N. Kent Gring
Attorney, Agent, or Firm—Patrick D. Kelly

[57] ABSTRACT

This invention relates to single-tool surgical instruments, such as scissors or forceps which do not pass through a channel in an operating laparoscope, which contain moving actuator parts at the end of a long slender shaft comprising a tube and a yoke. The actuator is operated by means of a handle assembly, which either forces or retracts an interior rod through a hollow shaft tube. These instruments can be disassembled to remove the interior rod from inside the shaft tube. This allows improved cleaning and removal of blood or tissue residues from the interior rod and shaft tube prior to sterilization, to provide for more effective and reliable sterilization of the components. The assembly includes a union coupling near the handle which allows the shaft tube to be disengaged from the handle without rotating either the interior rod or the shaft tube. After the shaft tube has been disengaged and pulled away slightly, the shaft and actuator assembly are rotated relative to the handle assembly. This unscrews the actuator assembly from the end of the interior rod. After the interior rod disengages from the actuator assembly, the shaft and actuator are pulled away from the handle assembly and interior rod. This exposes the interior rod and provides open access to the interior of the shaft tube, so that both components can be cleaned to remove any blood or tissue residue prior to sterilization. If desired, the actuator assembly can be removed from the end of the shaft tube, by removing a pivot screw, or by installing the actuator assembly in a shaft yoke device which can be removed from the end of the shaft tube.

6 Claims, 2 Drawing Sheets

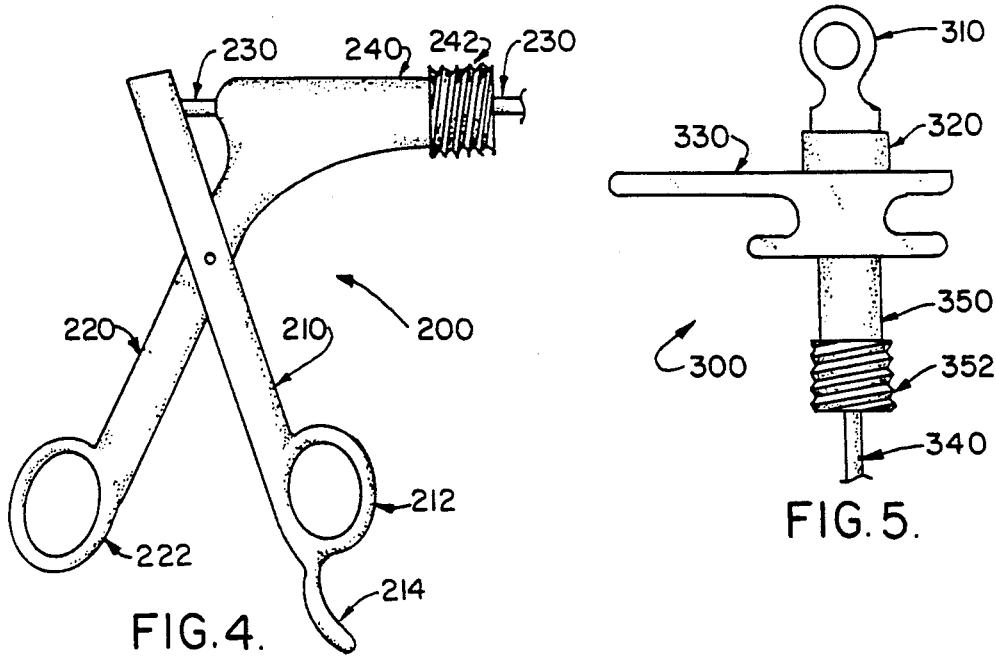
FIG. 4.
FIG. 5.
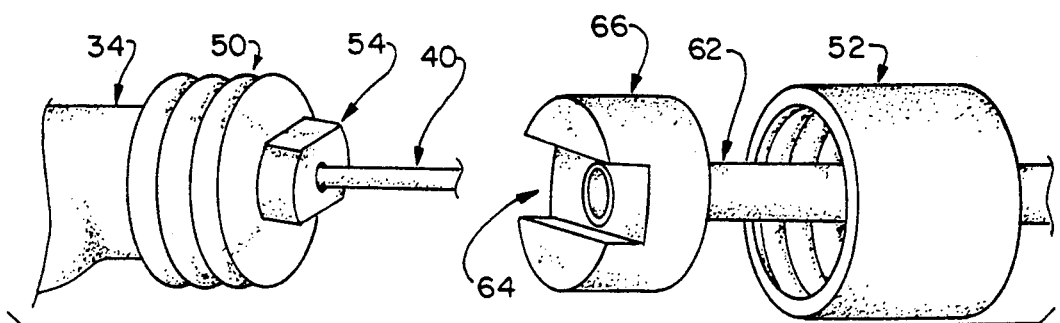
FIG. 6.
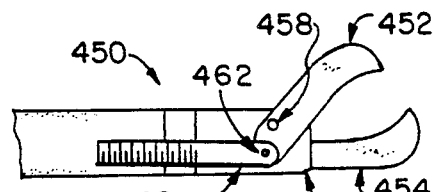
FIG. 7.
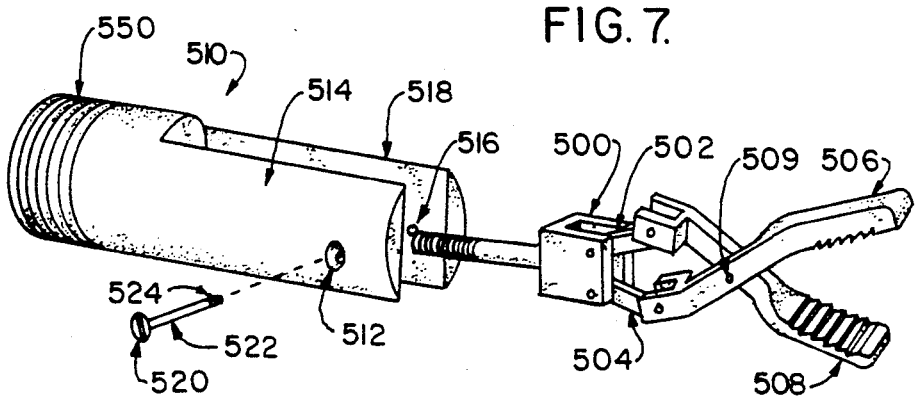
FIG. 8.

RIGID-SHAFT SURGICAL INSTRUMENTS THAT CAN BE DISASSEMBLED FOR IMPROVED CLEANING

BACKGROUND OF THE INVENTION

This invention is in the field of surgical instruments, and more particularly relates to "minimally invasive" surgical instruments such as laparoscopes and endoscopes.

As used herein, "minimally invasive surgery" (MIS) refers to surgery which utilizes instruments that penetrate the skin through a puncture or incision which is kept as small as possible given the needs of the operation. MIS devices include laparoscopic devices (which penetrate the peritoneal wall and enter the abdominal cavity; this includes instruments used in gynecology, and in sterlization procedures, and arthroscopic devices (which are used to operate on joints such as knees). Minimally invasive approaches and instruments have also been developed for thoracic surgery, including some types of cardiac surgery; although those uses are not as widespread as laparoscopic or arthroscopic surgery, such devices are gaining acceptance.

Minimally invasive surgery, as used herein, does not refer to endoscopic procedures, which normally do not puncture the skin. Endoscopic tools enter the body through a natural orifice; for example, bronchioscopes enter the chest through the nose or mouth, and proctoscopes enter the colon through the anus. In addition, as used herein, "minimally invasive surgery" excludes angioscopic devices pass through blood vessels. Endoscopic and angioscopic devices typically have flexible assemblies between the handle and the operating end, to allow the operating end to be pointed or twisted in any desired direction as it passes through channels or tunnels inside the body. Any such devices which have flexible shafts are not covered by the subject invention.

One class of devices which are used to manipulate tissue or bone during minimally invasive surgery have rigid shafts with a hand-operated handle at one end and an actuator (such as scissor blades or forceps jaws) at the other end. The rigid shaft allows the surgeon who is gripping the handle to have positive, firm control over the tissue that is being cut, pulled, sutured, or otherwise manipulated. Various rigid-shaft MIS devices are commercially available from companies such as Elmed (Addison, Ill.), Snowden-Pencer (Tucker, Ga.), and Wolf Medical Instruments (Rosemont, Ill.); these companies all publish catalogs showing photographs and other illustrations.

In general, rigid-shaft instruments used in MIS procedures can be grouped into either of two categories. In one category, which is not involved in this invention, an operating instrument (such as scissors or grasping forceps) with a very slender shaft is inserted through a channel (often called a probe channel) in a larger shaft which also carries a light source and/or a fiber optic cable for viewing. For example, a typical operating laparoscope has a shaft with an outside diameter of 10 millimeters (mm), and a probe channel with an inside diameter of 5 mm for insertion of an operating tool. These devices, which allow certain types of surgical procedures to be carried out through a single skin puncture, are sometimes called "operating laparoscopes," since they include both the scopic (viewing) components and the operating instrument. These devices are not covered by the subject invention.

The second category, covered by the subject invention, involves simpler operating tools which do not pass through the same shaft with a light source or viewing component. These are sometimes called "double puncture" instruments, since they normally can be used only in an operation that involves at least two skin punctures (i.e., the operating instrument passes through one skin incision, while the light source and a viewing instrument must pass through a second incision). As used herein, these devices are referred to as "single-tool rigid-shaft" (STRS) instruments; the phrase "single tool" distinguishes them from operating laparoscopes and other devices having more than one tool or function, while the phrase "rigid shaft" distinguishes them from endoscopes and other devices that are flexible rather than rigid.

A typical STRS device will have a shaft diameter of 3, 5, or 10 millimeters (mm), and an overall length of somewhere between 30 to 50 cm. The handles of most such devices usually fall into either of two categories; one category is usually called "scissor" or "ring" handles, while the other category is referred to herein as "plunger" handles. As implied by the name, scissor handles resemble the handles of a pair of scissors, where the two pieces of the handle are connected by a single pivot point. The pivot (usually a screw or rivet) effectively creates a lever system, with handle components (usually shaped as rings, so that a finger and a thumb can be inserted through the rings without risk of slippage) on one side of the pivot and lever components on the other side of the pivot. Plunger handles involve an internal component which slides through the shaft of a second external component, comparable to a large syringe. In one type of scissor handle arrangement, shown in FIG. xxx, closure of the ring portions causes closure of the lever components. In a different scissor handle arrangement, shown in FIG. xxx, closure of the ring portions causes the lever portions to open rather than close. In a plunger handle, an internal component slides through the shaft of an external component, in a manner comparable to a syringe. Specialized handles are available with devices such as rachets to hold the actuators firmly closed (or open), and spring-loaded arrangements that cause the actuators to remain closed until opened by the surgeon.

As used herein, "actuator" refers to the portion of a surgical instrument that actually contacts and manipulates tissue in a patient (or animal). Several types of common actuators are scissors, grasping forceps, and biopsy forceps. Scissors use sharpened blades to cut tissue in roughly the same manner as conventional scissors, although blade shapes vary. Grasping forceps include devices which grasp but do not intentionally cut or puncture tissue; for example, forceps with broad jaws (resembling pliers) are used for tasks such as pulling out gall bladders that have been surgically cut away from the liver, while forceps with narrow jaws can be used to manipulate a needle during suturing. Biopsy forceps use blade, scraper, hook, or punch arrangements to remove a small piece of tissue from a patient's body for analysis. These actuators are shown in catalogs published by suppliers such as Elmed, Snowden-Pencer, or Wolf.

The shaft of a typical single-channel rigid-shaft (STRS) instruments includes a hollow cylindrical shaft, which encloses a solid bar. The solid bar is connected at the forward or operating end to the actuator device (i.e., the scissor blades or forcep jaws), and at the rear or handle end to one piece of the handle assembly. When the handle is operated, the solid bar slides through the shaft tube and operates the actuator assembly. Various types of actuator assemblies are used. For example, the solid bar that passes through the shaft tube can be coupled, via a pivot, to one of the blades or jaws in a scissors or forceps assembly; the other blade, jaw, or anvil of the scissors remains rigidly attached to the end of the shaft tube, and the single movable blade or jaw interacts with the fixed component to create the desired result. Alternately, more complex arrangements are also available to cause symmetric (or non-symmetric) movement of both blades or jaws.

One of the most important problems facing endoscopic surgery involves contaminated and inadequately sterilized instruments, which can infect patients. Various articles and patents which discuss the various techniques used for sterilizing laparoscopes (and endoscopes) include Marshburn et al, *J. of Reproductive Medicine* 36: 483-487 (1991), U. Frank and F. Daschner, *Endoscopy* 21: 276-279 (1989), and G. Gorse and R. Messner, *Infect. Control Hosp. Epidemiol.* 12: 289-296 (1991). Although various techniques (such as steam sterilization, and chemicals such as glutaraldehyde) are widely used, they are inadequate to reliably kill all the bacteria, bacterial spores, and viruses that can be present in blood and tissue residues that infiltrate into surgical devices.

Bacterial spores deserve particular attention, since they pose a major threat of infection. In general, spores are dehydrated bacterial particles that are enclosed in a relatively hard casing. They are analogous to hard-shell plant seeds that can pass through the entire digestive tract of a bird or animal and emerge still capable of sprouting and growing a healthy plant. In the same way, bacterial spores have evolved in a way that allows them to resist and survive hostile conditions. This often enables substantial numbers of spores to survive sterilization using chemicals such as glutaraldehyde, or brief autoclaving, if the spores are coated by blood or tissue residues that shelter and protect the spores. If prolonged heating is used, it can damage the temper and weaken the steel used in surgical instruments.

In an effort to provide better sterilization of laparoscopes, several techniques have been developed. For example, so-called operating laparascopes (which have multiple channels in a single shaft) are designed in a way that allows a surgical instrument (such as scissors or forceps) to be removed from the probe channel. This allows the exterior of the instrument to be thoroughly wiped off, and it allows the probe channel in the large laparoscopic shaft to be rinsed out with high-pressure water. However, this technique is not available for single-channel rigid-shaft (STRS) instruments as defined above, since such devices are not inserted through a probe channel in a larger device.

Some rigid-shaft instruments have been developed which provide a rinsing channel through the shaft of the device. The rinsing channel is opened by removing inlet and outlet plugs or other devices at each end; water is then forced into the inlet end, and it passes through the interior of the shaft tube while the solid actuator bar remains inside the tube. This is partially but not completely effective in removing blood and tissue residues from inside the shaft of the device. It also suffers from various other problems; for example, in the often hurried and crowded environment of a hospital, any small components that are temporarily removed from a larger instrument can be misplaced and lost.

The subject invention discloses an improved method of constructing single-channel rigid-shaft (STRS) instruments for minimally invasive surgery. In this invention, a method is provided for disassembling the instrument so that the interior rod can be removed from inside the shaft tube. This allows all surfaces of both the interior rod and the hollow shaft tube to be rinsed, wiped, or brushed until they are completely clean. This removes all blood and tissue residue from the disassembled components, so that when the components are sterilized (either assembled or disassembled), the sterilization is much more effective and reliable.

Accordingly, one object of this invention is to disclose a single-channel rigid-shaft minimally invasive surgical instrument which can be disassembled for improved cleaning and sterilization. Another object of this invention is to disclose a method of sterilizing a single-channel rigid-shaft instrument which can be disassembled to remove the interior rod from the outer shaft tube.

SUMMARY OF THE INVENTION

This invention relates to single-tool surgical instruments, such as scissors or forceps which do not pass through a channel in an operating laparoscope, which contain moving actuator parts at the end of a long slender shaft comprising a tube and a yoke. The actuator is operated by means of a handle assembly, which either forces or retracts an interior rod through a hollow shaft tube. These instruments can be disassembled to remove the interior rod from inside the shaft tube. This allows improved cleaning and removal of blood or tissue residues from the interior rod and shaft tube prior to sterilization, to provide for more effective and reliable sterilization of the components. The assembly includes a union coupling near the handle which allows the shaft tube to be disengaged from the handle without rotating either the interior rod or the shaft tube. After the shaft tube has been disengaged and pulled away slightly, the shaft and actuator assembly are rotated relative to the handle assembly. This unscrews the actuator assembly from the end of the interior rod. After the interior rod disengages from the actuator assembly, the shaft and actuator are pulled away from the handle assembly and interior rod. This exposes the interior rod and provides open access to the interior of the shaft tube, so that both components can be cleaned to remove any blood or tissue residue prior to sterilization. If desired, the actuator assembly can be removed from the end of the shaft tube, by removing a pivot screw, or by installing the actuator assembly in a shaft yoke device which can be removed from the end of the shaft tube.

BRIEF DESCRIPTION OF THE FIGURES

FIG. 4 depicts a handle assembly with crossing handles, where closure of the gripping rings causes forward motion of the interior rod.

FIG. 5 depicts a plunger-type handle assembly.

FIG. 6 is a detail drawing of a union coupling which allows the shaft and actuator to be attached to or disengaged from a handle assembly, with a key-and-slot arrangement that prevents rotation of the shaft and actuator when they are affixed to the handle.

FIG. 7 is a detail drawing of a single-motion actuator, where only one blade or jaw of the actuator moves while the other blade or jaw is rigidly affixed to the shaft.

FIG. 8 depicts an actuator assembly which can be removed from the shaft yoke and shaft by removing a threaded screw that serves as the center pivot in the actuator. This drawing also depicts threads on the back end of the shaft yoke, which would allow the shaft yoke and actuator to be screwed into or out of the shaft tube.

DESCRIPTION OF THE PREFERRED EMBODIMENTS

Figure 1:
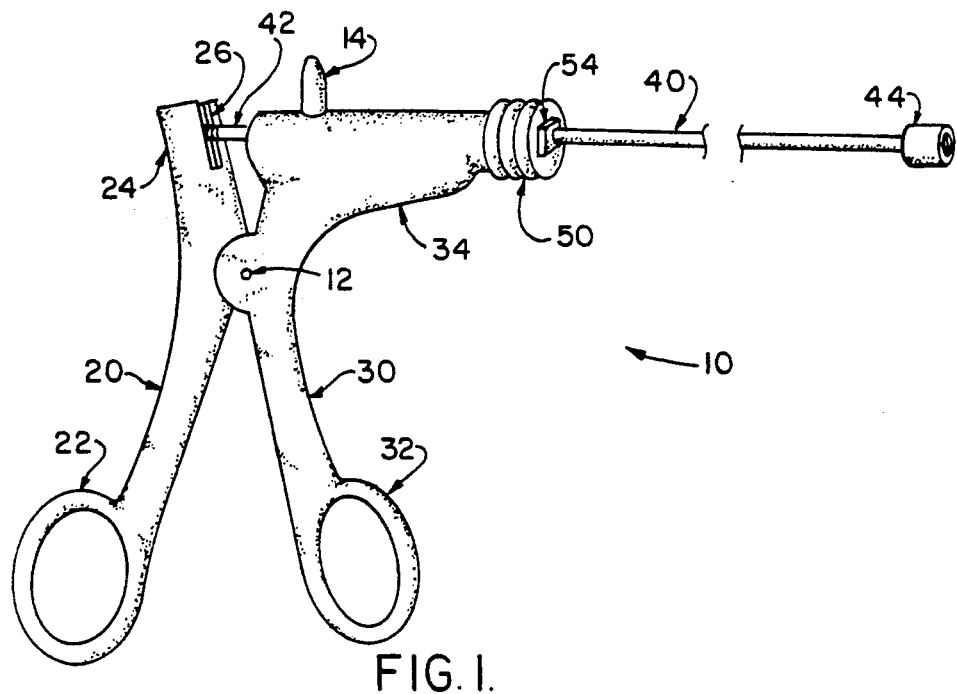
FIG. 1 is a perspective view of a handle and interior rod assembly, after the shaft and actuator have been removed.

Referring to the drawings, FIG. 1 depicts a handle-and-rod assembly 10. This handle assembly is coupled to a shaft-and-actuator assembly 60 (shown in FIG. 2) to create a complete instrument 100, shown in FIG. 3.

Handle and rod assembly 10 comprises a pivot 12 (which can be a conventional screw or rivet) which holds together a first handle component 20 having a gripping ring 22 and a lever end 24 with groove 26, and a second handle component 30 having a gripping ring 32 and a handle barrel 34. The two handle components 20 and 30 interact in a manner comparable to scissor handles. A finger or thumb is inserted by the surgeon into gripping rings 22 and 32. When the surgeon closes the two gripping rings together, the lever end 24 of the handle component 20 is pulled away from the handle barrel 34. This action exerts a forceful pull on the handle end 42 of interior rod 40; it pulls it toward the rear (any references herein to forward or rear assume that the actuator is at the forward end of the instrument, while the handles are at the rear end). The forward end of rod 40 is coupled to an internally threaded sleeve 44, which has an outside diameter slightly smaller than the inside diameter of the shaft tube 62.

In order to avoid any bending force that might warp the handle end 42 of interior rod 40, the handle end 42 of rod 40 can be threaded and screwed into a spherical or other appropriately shaped sliding nut which can slide up and down slightly within groove 26 in lever end 24. Alternately, a flexible or jointed rod can be used so long as it is capable of generating force in both directions (e.g., tension to pull the actuator jaws or blades closed, and pressure to force the jaws open again). Unless carefully constrained in a relatively tight channel (which normally would not be desirable), a thin cable would not be adequate to provide sufficient pushing force; however, a stiff cable or a linked or jointed structure would be adequate to serve as the interior rod. In general, a solid rod having a circular cross-section and a smooth shaft except for threads at one or both ends is preferable, since it is simple, inexpensive, and easy to clean.

Various other handle arrangements can be used if desired. For example, in the scissors-type handle assembly 200 shown in FIG. 4, the two handle components 210 and 220 cross each other in an X-configuration. Closure of the gripping rings 212 and 222 causes the interior rod 230 to be pushed forcefully through the handle barrel 240 and threaded coupling 242, and through the shaft tube when the instrument is assembled. Gripping ring 212 is accompanied by an arc attachment 214 which allows a second finger to apply additional squeezing pressure on the handle assembly. Alternately, in a plunger-type handle assembly 300 as shown in FIG. 5, a plunger 310 passes through cylinder 320 which is mounted in handle 330, which is shaped in a manner allowing it to be gripped firmly for either pulling or pushing. Pressure applied to the plunger 310 forces an interior rod 340 through handle barrel 350 and threaded coupling 352.

Alternately, a handle similar to the handles used in certain types of biopsy forceps can be provided, having a detachable joint for the actuator rod near the front end of the handle barrel. In the prior art, these forceps allow a single handle assembly to be used with different types of actuators, such as straight-jaw and angled-jaw forceps. However, they do not provide for removal of the interior rod from the shaft tube and actuator.

In FIG. 1, an exposed metallic protrusion 14 can serve as an electrode to allow the actuator tip (or an exposed portion thereof) to be used for cauterization, which is commonly used to close small blood vessels if bleeding is encountered. If this approach is used, the remainder of the handle assembly and the shaft tube should both be coated with an electrically insulating material such as plastic, to channel the electrical current through the actuator tip.

An externally threaded male coupling 50 is securely affixed (such as by welding) to the front end of the handle barrel 34. As indicated by FIG. 6, male coupling 50 is screwed into an internally threaded female coupling 52, which can slide and rotate freely on the outside of the shaft 62 of shaft assembly 60. This type of juncture is often called a union joint. The male coupling 50 is fitted with a non-circular protrusion 54 (also called a key) which fits into an accommodating slot 64 in a nut 66 which is securely affixed, in a non-rotating manner, to the shaft tube 62.

If desired, the slot-and key assembly can be designed to yield and rotate at a torsion level which is lower than the torsional strength of the actuator jaws. If a small piece such as a forcep jaw or a scissor blade breaks off from the end of an instrument during minimally invasive surgery, it can be very difficult to retrieve it from inside the patient's body. To minimize the risk of such an occurrence, the slot-and-key assembly can be designed to yield and rotate at a torsion level which is lower than the torsional strength of the actuator jaws. This can be done in any of several manners, by using a suitable geometric configuration (such as a six or eight-sided key with slightly rounded corners), by using a spring-loaded device (such as a flat metallic leaf or a spring-mounted ball), or by using a relatively soft material such as a plastic or an elastomeric coating, in either the key 54 or the slot 64.

Figure 2:
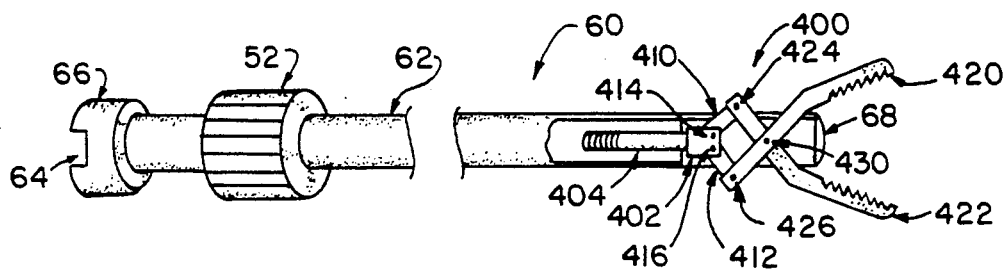
FIG. 2 is a partial cutaway view of a shaft and actuator assembly (forceps jaws) which have been removed from a handle assembly.
Figure 3:
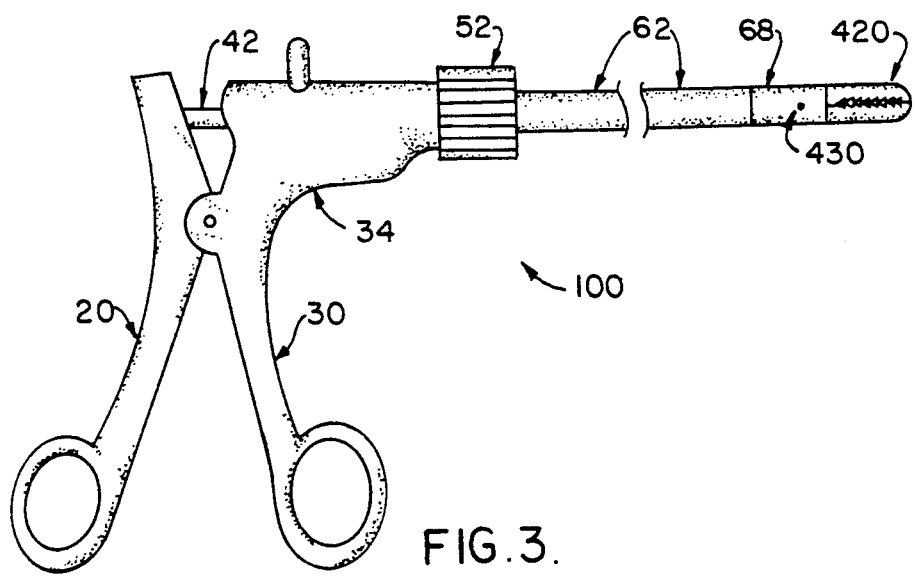
FIG. 3 depicts a complete surgical tool, which is assembled by connecting a handle and rod assembly to a shaft tube and actuator assembly.

A double-motion actuator assembly 400, which is shown in FIG. 2 and in more detail in FIG. 8, is fitted into the slot of a shaft yoke 68. Actuator assembly 400 comprises an actuator yoke 402 and various levers, pivots, etc. In the actuator assembly shown in FIGS. 2 and 8, actuator yoke 402 comprises a U-shaped piece of metal welded to a threaded actuator rod 404, which will be screwed into sleeve 44 affixed to the tip of interior rod 40. If desired, actuator yoke 402 can be made of a single piece of metal, by milling a slot in the front end and either drilling and internally threading a hole on the back end (which would allow an externally-threaded rod to be screwed directly into the back of the yoke, without requiring an additional sleeve at the end of the rod), or by providing external threads directly on the back end of a single-piece actuator yoke.

Two lever arms 410 and 412 are secured to actuator yoke 402 in a rotatable manner by pivots 414 and 416. Each lever arm is connected at its forward end to a jaw component 420 or 422, by means of rotatable pivots 424 or 426. A center pivot 430 which passes all the way from one arm of the shaft yoke 68 to the other side couples the two jaws 420 and 422 to each other and to the two arms of the shaft yoke 68. When in use, the center pivot 430 can be thought of as a fixed point. When the threaded rod 404 and yoke 402 are pulled backward (i.e., toward the handle), the lever arms 410 and 414 cause the jaw components 420 and 422 to be pulled toward a closed position, which allows them to securely grip a piece of tissue inside the patient's body.

A single-motion actuator assembly 450 is shown in FIG. 7. This type of actuator is widely used in scissors (as shown in FIG. 7) and in biopsy forceps. In this type of actuator, only the upper blade 452 moves, while lower blade 454 is rigidly affixed to the end of the shaft yoke 456. The moving blade 452 is controlled by an actuator yoke 460 which is attached near the rear end of blade 452 by means of a pivot 462. The blade is mounted to the shaft yoke 456 via a pivot 458.

The shaft tube can be fabricated in any of several suitable ways. In one preferred method, shaft yoke 68 is made by milling a slot in the end of a solid cylinder made of a hard metal such as stainless steel. The arms that remain on each side of the milled slot will serve as the yoke arms to hold the actuator assembly. A small hole for the center pivot 430 is drilled through each yoke arm, and the hole is countersunk slightly on both sides of the shaft yoke. A larger hole is drilled through the rear end of shaft yoke 68, to allow passage of the actuator rod 404. Shaft yoke 68 is then welded to the end of a hollow stainless steel tube 62 having a desired length. Either before or after the shaft tube 62 is welded to the shaft yoke 68, the actuator assembly 400 is inserted into the shaft yoke, and a piece of stiff wire which will serve as pivot 430 is inserted through pivot holes in both yoke arms and the jaw or blade components. Once in place, the wire is cut to a suitable length, then it is peened at each end with a rounded hammer to create a rivet that cannot slide in either direction. The rivet heads are polished on both sides of the yoke, to make sure that no spurs project on either side. This completes the fabrication of the shaft and actuator assembly 60.

In order to attach the shaft and actuator assembly 60 to the handle and rod assembly 10, the tip of rod 40 (including a threaded sleeve 44) is inserted into the rear opening of shaft tube 62. The rings 22 and 32 of the handle assembly are manually held open, to ensure that the rod 40 will be extended a maximal distance into the shaft tube 62. The rod 40 and shaft 62 have accommodating lengths, so that if rod 40 is inserted all the way into shaft tube 62 while the handles are held open, the internally threaded sleeve 44 will reach and engage the externally threaded actuator rod 404. During this step of the assembly procedure, slot 64 in nut 66 does not yet engage protrusion 54 on the handle assembly. This allows the shaft and actuator assembly 60 to be rotated relative to the handle, causing the threaded actuator rod 404 to become firmly screwed into sleeve 44. This completes the first step of the assembly procedure. If desired, sleeve 44 can be provided with a flared opening, to facilitate seating of the threaded components and engagement of the threads during assembly.

In the second step, shaft tube 62 is pushed toward the handle, far enough so that the slot 64 in nut 66 engages the protrusion (key) 54 on the handle assembly. When those two pieces have been pushed firmly against each other, female coupling 52 (which can rotate freely on the outside of the shaft 62) is screwed onto the threaded male coupling 50 which is affixed to the handle assembly. This completes the assembly of the instrument.

In order to disassemble the instrument, the steps are reversed; the female coupling 52 is unscrewed from the handle assembly, the shaft assembly is pulled forward to disengage slot 64 from protrusion 54, and the shaft assembly is rotated to unscrew actuator rod 404 from the sleeve 44 at the end of rod 40.

The two subassemblies are then pulled completely apart, removing the rod 40 and the threaded sleeve 44 from inside the shaft tube 62, to provide access to the internal surfaces. This allows cleaning of the shaft and rod components in a manner that is substantially improved over other single-tool rigid-shaft devices of the prior art. The interior rod 40 and sleeve 44 are completely exposed; in addition, the shaft 62 is open at one end, so that a bottle brush or other tool can be inserted and used to scrape blood and tissue residue out from inside the shaft 62.

The threaded end of actuator rod 404 will limit the reach of a blunt-ended brush. However, that does not pose a serious problem. If jaw components 420 and 422 are held open (i.e., pulled apart from each other) during cleaning, this will pull actuator rod 404 forward, and the threaded tip of rod 404 will protrude only a short distance (such as about 1 centimeter or less) into the inside of the shaft. A cleaning brush or other scraping instrument can be used which has an annular tip, or which has end-bristles that extend lengthwise about 1 cm beyond the solid end of the bristle-holder. This will allow the annular tip or end-bristles to extend beyond the threaded end of the actuator rod 404 and reach all surfaces inside the shaft tube 62.

This particular embodiment offers several advantages. No small components are removed from the two large subassemblies, so there is no risk of losing any small components such as screws or rinsing channel plugs. The instrument is disassembled into only two subassemblies, and all steps are quick (disassembly or assembly require only about ten to fifteen seconds each) and simple (assembly and disassembly can be taught in about two minutes). In addition, no screwdrivers, wrenches, or other tools are required; assembly and disassembly can be done completely by hand. Also, if the tip of the shaft tube is welded to the end of the tube, it can provide greater strength than other assemblies where the tip can be removed from the end of the tube.

Optionally, two methods are available for removing the actuator assembly from the tip of the shaft; both are depicted in FIG. 8, although it is presumed that only one method would be provided on any particular instrument. In one method, shown in FIG. 8, actuator yoke 500 containing lever arms 502 and 504 coupled to jaws 506 and 508 is secured inside the slot of a shaft yoke 510 by means of a threaded center-pivot screw 520. Preferably, pivot screw 520 should not be threaded over its entire length; instead, the screw should have a smooth shaft 522 and a threaded tip 524. This will allow the smooth shaft to pass through a countersunk smooth-bore hole 512 in shaft arm 514 and through smooth-bore holes 509 in jaws 506 and 508. The threaded tip 524 of screw 520 will screw into a threaded hole 516 in shaft yoke arm 518. The smooth shaft of pivot screw 520 will provide a smooth pivoting surface for the actuator jaws 506 and 508. To clean the assembly between uses, the shaft and actuator are disengaged from the handle assembly, then pivot screw 520 is removed. This will release the actuator assembly yoke 500 from the shaft yoke 510, allowing unimpeded access to all actuator assembly components and to the interior surfaces of the shaft.

In an alternate embodiment, also depicted in FIG. 8, shaft yoke 510 can be detached from a shaft tube by means such as providing external threads 550 on the back end of the shaft yoke 510, and by providing accommodating internal threads inside the end of a shaft tube. If a threaded engagement is used, it should be accompanied by a means to prevent rotation of the actuator assembly on the shaft tube during an operation, such as a screw mounted radially on one side of the shaft. Alternately, a non-rotating engagement can be used, such as a bayonet-type coupling, so long as it does not create significant protrusions which extend beyond the outside diameter of the shaft.

The actuator assemblies of this invention require a significant but not excessive level of miniaturization. Except for features that allow disassembly and improved cleaning of the instrument, items such as forceps jaws and lever arms are identical to similar items used in prior art devices which are commercially available. The so-called "double puncture" forceps or scissor devices of the prior art, which cannot be disassembled, typically have diameters of 3, 5, or 10 millimeters. Typical lever arm components in such actuator assemblies are about 2 to 3 mm wide and somewhat less than 1 mm thick at the narrowest point; these dimensions can be achieved without difficulty by conventional machining techniques. For example, a rack or array of a dozen or more lever arms with pivot holes can be laser-cut using a flat sheet of metal; subsequently, each lever arm is broken off from the rack, and the lever arm is pressed briefly against a polishing wheel to remove any burrs. Pivots are typically provided by inserting a stiff stainless steel wire having a desired thickness (such as about 0.7 mm) through the holes in the lever arms, and cutting off the ends of the wire after insertion; the wire can be peened at either or both ends to ensure that it cannot slide out of the pivot hole. All other components, including unfinished forged ring handles and shaft tubes, can be purchased from commercial suppliers. Welding, soldering, or brazing is done using a material such as silver solder which has suitable strength and which is suitable for contact with tissue and biological fluids.

Thus, there has been shown and described a new and useful type of minimally invasive surgical instrument that can be disassembled for improved cleaning and sterilization. Although this invention has been exemplified for purposes of illustration and description by reference to certain specific embodiments, it will be apparent to those skilled in the art that various modifications and alterations of the illustrated examples are possible. Any such changes which derive directly from the teachings herein, and which do not depart from the spirit and scope of the invention, are deemed to be covered by this invention.

We claim:

1. A surgical instrument comprising an operable handle assembly, a rigid shaft comprising a shaft tube and a shaft yoke which is affixed to one end of the shaft tube in a non-rotatable manner, an internal rod, and an actuator assembly, wherein:
   a. the operable handle assembly comprises a first gripping component which is affixedly attached to a handle barrel, and a second gripping component which is movable relative to said handle barrel and which is coupled to the interior rod in a manner such that the interior rod moves relative to the handle barrel when the handle assembly is operated;
   b. the internal rod passes through the shaft tube when the surgical instrument is assembled, wherein a first end of the interior rod is coupled to the second gripping component of the operable handle assembly and a second opposed end of the interior rod is threadedly and detachably coupled to an actuator yoke;
   c. The shaft tube has an outside diameter of about 10 millimeters or less and a length of about 20 centimeters or more; and wherein the shaft tube is reversibly coupled at one end of said shaft tube to the handle barrel, by means of an attachment device that does not require rotation of the shaft relative to the handle assembly; and wherein the shaft yoke is positioned at a second opposed end of said shaft tube and is coupled to the actuator assembly;
   d. the actuator assembly comprises (1) a actuator yoke which is movable relative to the shaft and which is threadedly and detachably coupled to the internal rod when the instrument is assembled, which can be uncoupled from the internal rod, thereby allowing removal of the internal rod from inside the shaft when the surgical instrument is disassembled; (2) at least two actuator components capable of opening and closing relative to useful manner during surgery, wherein at lest one movable actuator component is coupled via a pivot to the actuator yoke in a manner such that when the internal rod and actuator yoke are moved relative to the shaft due to operation of the handle assembly, at least one movable actuator component moves in a desired direction that allows a desired tissue manipulation,
   wherein the surgical instrument can be disassembled, for cleaning purposes, by steps consisting essentially of: (a) disengaging the operable handle assembly from the shaft; (b) unscrewing the actuator yoke from the internal rod; and (c) removing the interior rod from inside the shaft, and wherein disassembly of other component parts is not necessary to allow disassembly, cleaning, and sterilization of components which enter a patient's body during a surgical procedure.

2. The surgical instrument of claim 1, wherein the actuator assembly is affixed to the shaft yoke by means of a nonremovable rivet.

3. The surgical instrument of claim 2, wherein the shaft yoke is welded to the shaft, so that no small parts are detached from the instrument during disassembly or cleaning.

4. The surgical instrument of claim 2, wherein the shaft yoke is detachably coupled to the shaft tube in a manner which allows the shaft yoke and actuator assembly to be detached from the shaft tube for cleaning purposes.

5. The surgical instrument of claim 1, wherein the actuator assembly is affixed to the shaft yoke by means of a pivot screw which allows the actuator assembly to be removed from the shaft yoke for cleaning purposes.

6. A surgical instrument comprising an operable handle assembly having two gripping components which are movable relative to each other; a rigid shaft comprising a hollow shaft tube; an actuator assembly having at least one movable component adapted to manipulating bodily tissue during a surgical operation, and a rod which is coupled at a first end to the operable handle assembly and which passes through the hollow shaft tube and which is detachably coupled at a second opposed end of the rod to the actuator assembly, wherein the rod moves relative to the shaft and causes movement of at least one movable component in the actuator assembly when the handle assembly is operated;

and wherein the shaft tube is reversibly coupled at one end of said shaft tube to the handle assembly;

and wherein the actuator assembly is affixed to an opposed end of the shaft tube in a non-rotatable manner;

and wherein the actuator assembly is threadedly and detachably coupled to the rod when the instrument is assembled, in a manner which allows the actuator assembly to be detached from the rod after the shaft tube has been disengaged from the handle assembly, thereby allowing the handle assembly to be completely detached form the shaft and allowing the rod to be completely removed from inside the shaft, so that the rod and any interior surfaces of the shaft tube are exposed for cleaning and sterilization, and wherein disassembly of other component parts is not necessary to allow disassembly, cleaning, and sterilization of components which enter a patient's body during a surgical procedure.

* * * * *